United States Patent
Kurahashi

(10) Patent No.: US 9,012,361 B2
(45) Date of Patent: Apr. 21, 2015

(54) COMPOSITION AND METHOD FOR CONTROLLING PESTS

(75) Inventor: Makoto Kurahashi, Hyogo (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/518,101

(22) PCT Filed: Dec. 22, 2010

(86) PCT No.: PCT/JP2010/073845
§ 371 (c)(1),
(2), (4) Date: Jul. 6, 2012

(87) PCT Pub. No.: WO2011/083745
PCT Pub. Date: Jul. 14, 2011

(65) Prior Publication Data
US 2012/0264602 A1    Oct. 18, 2012

(30) Foreign Application Priority Data
Jan. 6, 2010   (JP) ................... 2010-001042

(51) Int. Cl.
*A01P 7/02*    (2006.01)
*A01P 7/04*    (2006.01)
*A01C 1/06*    (2006.01)
*A01P 3/00*    (2006.01)
*A01N 43/90*   (2006.01)
*A01P 5/00*    (2006.01)
*A01N 43/78*   (2006.01)

(52) U.S. Cl.
CPC ............... *A01N 43/78* (2013.01); *A01N 43/90* (2013.01)

(58) Field of Classification Search
None
See application file for complete search history.

(56) References Cited

U.S. PATENT DOCUMENTS

| | | | |
|---|---|---|---|
| 5,514,643 A | 5/1996 | Rew et al. | |
| 2008/0200334 A1 | 8/2008 | Tormo I Blasco et al. | |

FOREIGN PATENT DOCUMENTS

| | | |
|---|---|---|
| EP | 0 639 574 | 2/1995 |
| JP | 2005-350387 | 12/2005 |
| JP | 2005350387 | * 12/2005 |
| JP | 2007-246495 | 9/2007 |
| JP | 2007-246496 | 9/2007 |
| JP | 2008-501664 | 1/2008 |
| JP | 2008-521761 | 6/2008 |
| WO | 2005/120232 | 12/2005 |
| WO | 2008/077926 | 7/2008 |
| WO | WO2008/077926 | * 7/2008 |

OTHER PUBLICATIONS

JP2005350387 Machine Translation, accessed Aug. 13, 2013.*
Written Opinion issued Mar. 8, 2011 in International (PCT) Application No. PCT/JP2010/073845, of which the present application is the national stage.
International Search Report issued Mar. 8, 2011 in International (PCT) Application No. PCT/JP2010/073845, of which the present application is the national stage.
Office Action issued Aug. 12, 2013 in Chinese Application No. 201080060685.9, with English translation.
International Search Report issued Mar. 8, 2012 in International (PCT) Application No. PCT/JP2010/073845, of which the present application is the national stage.
"The Pesticide Manual—14$^{th}$ edition", published by The British Crop Protection Council (BCPC), ISBN1901396142, pp. 3-5, 400-403, 2006.
Second Office Action issued Mar. 28, 2014 in corresponding Chinese patent application No. 201080060685.9 with English translation.
English translation of Taiwanese Office Action issued Aug. 8, 2014 in counterpart Taiwanese Patent Application No. 099146990.
Russian Office Action issued Oct. 17, 2014 in corresponding Russian Patent Application No. 2012133442 with English translation.
Ukrainian Office Action issued Sep. 11, 2014 in counterpart Ukrainian Application No. 201209495 with English translation.
Taiwanese Office Action issued Aug. 8, 2014 in counterpart Taiwanese Application No. 099146990.
Japanese Office Action issued Sep. 30, 2014 in corresponding Japanese Patent Application No. 2010-287409 with English translation.
Patent Examination Report No. 1 issued Dec. 4, 2014 in corresponding Australian Application No. 2010340508.

* cited by examiner

*Primary Examiner* — Kortney L Klinkel
*Assistant Examiner* — Melissa Javier
(74) *Attorney, Agent, or Firm* — Wenderoth

(57) ABSTRACT

The present invention provides: a composition for controlling pests comprising, as active ingredients, ethaboxam and avermectin; a method for controlling pests which comprises applying effective amounts of ethaboxam and avermectin to a pest, a plant or soil for growing plant; and so on.

4 Claims, No Drawings

COMPOSITION AND METHOD FOR CONTROLLING PESTS

TECHNICAL FIELD

The present invention relates to a composition for controlling pests and a method for controlling pests.

BACKGROUND ART

Known as active ingredients of pests controlling agents have been ethaboxam with fungicidal activity (see, for example, US Patent Publication No. 5514643) and avermectin with insecticidal activity (see, for example, "The Pesticide Manual-14th edition" published by The British Crop Protection Council (BCPC), ISBN1901396142).

DISCLOSURE OF INVENTION

An object of the present invention is to provide a composition for controlling pests and a method for controlling pests, having excellent control efficacy for pests.

The present invention provides a composition for controlling pests and a method for controlling pests, which exert excellent control efficacy for pests by the combined use of ethaboxam and avermectin.

Specifically, the present invention provides:

[1] A composition for controlling pests comprising, as active ingredients, ethaboxam and avermectin;

[2] The composition according to [1], wherein a weight ratio of ethaboxam to avermectin is in the range of 1:0.01 to 1:50;

[3] A seed treatment agent comprising, as active ingredients, ethaboxam and avermectin;

[4] A plant seed treated with effective amounts of ethaboxam and avermectin;

[5] A method for controlling pests which comprises applying effective amounts of ethaboxam and avermectin to a pest, a plant or soil for growing plant; and

[6] Combined use for controlling pests of ethaboxam and avermectin; and so on.

The composition of the present invention exerts an excellent control efficacy for pests.

MODES FOR CARRYING OUT THE INVENTION

Ethaboxam for use in the composition for controlling pests of the present invention is a compound disclosed in US Patent Publication No. 5514643. The compound can be obtained from commercial agents or can be obtained by producing by the method described in the publication.

Avermectin for use in the composition for controlling pests of the present invention is a known compound and disclosed, for example, in "The Pesticide Manual-14th edition" published by The British Crop Protection Council (BCPC), ISBN1901396142, pp. 3. The compound can be obtained from commercial agents or can be obtained by producing by known methods.

In the composition for controlling pests of the present invention, the weight ratio of ethaboxam to avermectin is typically in the range of 1:0.01 to 1:50, preferably 1:0.05 to 1:20. When applied as a foliar spray, the weight ratio of ethaboxam to avermectin is typically in the range of 1:0.01 to 1:10, preferably 1:0.05 to 1:5. When used as a seed treatment agent, the weight ratio of ethaboxam to avermectin is typically in the range of 1:0.05 to 1:50, preferably 1:0.1 to 1:20.

The composition for controlling pests of the present invention may be a simple mixture of ethaboxam and avermectin. Alternatively, the composition for controlling pests is typically produced by mixing ethaboxam and avermectin with an inert carrier, and adding to the mixture a surfactant and other adjuvants as needed so that the mixture can be formulated into an oil agent, an emulsion, a flowable agent, a wettable powder, a granulated wettable powder, a powder agent, a granule agent and so on. The composition for controlling pests mentioned above can be used as a seed treatment agent as it is or added with other inert ingredients.

In the composition for controlling pests of the present invention, the total amount of ethaboxam and avermectin is typically in the range of 0.1 to 99% by weight, preferably 0.2 to 90% by weight.

Examples of the solid carrier used in formulation include fine powders or granules such as minerals such as kaolin clay, attapulgite clay, bentonite, montmorillonite, acid white clay, pyrophyllite, talc, diatomaceous earth and calcite; natural organic materials such as corn rachis powder and walnut husk powder; synthetic organic materials such as urea; salts such as calcium carbonate and ammonium sulfate; synthetic inorganic materials such as synthetic hydrated silicon oxide; and as a liquid carrier, aromatic hydrocarbons such as xylene, alkylbenzene and methylnaphthalene; alcohols such as 2-propanol, ethyleneglycol, propylene glycol, and ethylene glycol monoethyl ether; ketones such as acetone, cyclohexanone and isophorone; vegetable oil such as soybean oil and cotton seed oil; petroleum aliphatic hydrocarbons, esters, dimethylsulfoxide, acetonitrile and water.

Examples of the surfactant include anionic surfactants such as alkyl sulfate ester salts, alkylaryl sulfonate salts, dialkyl sulfosuccinate salts, polyoxyethylene alkylaryl ether phosphate ester salts, lignosulfonate salts and naphthalene sulfonate formaldehyde polycondensates; and nonionic surfactants such as polyoxyethylene alkyl aryl ethers, polyoxyethylene alkylpolyoxypropylene block copolymers and sorbitan fatty acid esters and cationic surfactants such as alkyltrimethylammonium salts.

Examples of the other formulation auxiliary agents include water-soluble polymers such as polyvinyl alcohol and polyvinylpyrrolidone, polysaccharides such as Arabic gum, alginic acid and the salt thereof, CMC (carboxymethyl-cellulose), Xanthan gum, inorganic materials such as aluminum magnesium silicate and alumina sol, preservatives, coloring agents and stabilization agents such as PAP (acid phosphate isopropyl) and BHT.

The composition for controlling pests of the present invention can protect plants from damages by the following pests (for example, arthropod pests such as insect pests and mite pests, nematodes and plant pathogens) which cause damages such as feeding or sucking to plants. Examples of arthropod pests and nematodes against which the composition for controlling pests of the present invention has control efficacy include the followings:

Hemiptera: planthoppers such as small brown planthopper (*Laodelphax striatellus*), brown rice planthopper (*Nilaparvata lugens*) and white-backed rice planthopper (*Sogatella furcifera*); leafhoppers such as green rice leafhopper (*Nephotettix cincticeps*) and green rice leafhopper (*Nephotettix virescens*); aphids such as cotton aphid (*Aphis gossypii*), green peach aphid (*Myzus persicae*), cabbage aphid (*Brevicoryne brassicae*), potato aphid (*Macrosiphum euphorbiae*), foxglove aphid (*Aulacorthum solani*), oat bird-cherry aphid (*Rhopalosiphum padi*) and tropical citrus aphid (*Toxoptera citricidus*); stink bugs such as green stink bug (*Nezara antennata*), bean bug (*Riptortus clavetus*), rice bug (*Leptocorisa* chinensis), white spotted spined bug (*Eysarcoris parvus*), brown marmorated stink bug (*Halyomorpha mista*) and tarnished plant bug (*Lygus lineolaris*); whiteflies such as greenhouse whitefly (*Trialeurodes vaporariorum*), sweetpotato whitefly (*Bemisia tabaci*) and silverleaf whitefly (*Bemisia argentifolii*); scales such as california red scale (*Aonidiella aurantii*), san jose scale (*Comstockaspis perniciosa*), citrus snow scale (*Unaspis citri*), red wax scale (*Ceroplastes rubens*) and cottony cushion scale (*Icerya purchasi*); lace bugs; and psyllids;

Lepidoptera: pyralid moths such as rice stem borer (*Chilo suppressalis*), yellow stem borer (*Tryporyza incertulas*), rice leafroller (*Cnaphalocrocis medinalis*), cotton leafroller (*Notarcha derogata*), indian meal moth (*Plodia interpunctella*), oriental corn borer (*Ostrinia furnacalis*), european corn borer (*Ostrinia nubilaris*), cabbage webworm (*Hellula undalis*) and bluegrass webworm (*Pediasia teterrellus*); owlet moths such as common cutworm (*Spodoptera litura*), beet armyworm (*Spodoptera exigua*), rice armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; Pieridae such as cabbage butterfly (*Pieris rapae*); tortricid moths such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), smaller tea tortrix (*Adoxophyes* sp.), oriental tea tortrix (*Homona magnanima*), apple tortrix (*Archips fuscocupreanus*), and codling moth (*Cydia pomonella*); leafblotch miners such as tea leafroller (*Caloptilia theivora*), and apple leafminer (*Phyllonorycter ringoneella*); fruitworm moths such as peach fruit moth (*Carposina niponensis*); lyonetiid moths such as *Lyonetia* spp.; tussock moths such as *Lymantria* spp., and *Euproctis* spp.; yponomeutid moths such as diamondback moths (*Plutella xylostella*); gelechiid moths such as pink bollworm (*Pectinophora gossypiella*), and potato tuberworm (*Phthorimaea operculella*); tiger moths such as fall webworm (*Hyphantria cunea*); and tineid moths such as casemaking clothes moth (*Tinea translucens*), and webbing clothes moth (*Tineola bisselliella*);

Thysanoptera: thrips (Thripidae) such as yellow citrus thrip (*Frankliniella occidentalis*), melon thrip (*Thrips parmi*), yellow tea thrip (*Scirtothrips dorsalis*), onion thrip (*Thrips tabaci*), flower thrip (*Frankliniella intonsa*), and tobacco thrip (*Frankliniella fusca*);

Diptera: house fly (*Musca domestica*); common house mosquito (*Culex pipiens pallens*); common horse fly (*Tabanus trigonus*); onion maggot (*Hylemya antiqua*); seedcorn maggot (*Hylemya platura*); hyrcanus group mosquito (*Anopheles sinensis*); leaf miners such as rice leafminer (*Agromyza oryzae*), rice leafminer (*Hydrellia griseola*), rice stem maggot (*Chlorops oryzae*) and legume leafminer (*Liriomyza trifolii*); melon fly (*Dacus cucurbitae*); and Mediterranean fruit fly (*Ceratitis capitata*);

Coleoptera: twenty-eight-spotted ladybird (*Epilachna vigintioctopunctata*), cucurbit leaf beetle (*Aulacophora femoralis*), striped flea beetle (*Phyllotreta striolata*), rice leaf beetle (*Oulema oryzae*), rice curculio (*Echinocnemus squameus*), rice water weevil (*Lissorhoptrus oryzophilus*), boll, weevil (*Anthonomus grandis*), azuki bean weevil (*Callosobruchus chinensis*), hunting billbug (*Sphenophorus venatus*), Japanese beetle (*Popillia japonica*), cupreous chafer (*Anomala cuprea*), corn root worms (*Diabrotica* spp.), Colorado beetle (*Leptinotarsa decemlineata*), click beetles (*Agriotes* spp.), cigarette beetle (*Lasioderma serricorne*), varied carper beetle (*Anthrenus verbasci*), red flour beetle (*Tribolium castaneum*), powder post beetle (*Lyctus brunneus*), white-spotted longicorn beetle (*Anoplophora malasiaca*), and pine shoot beetle (*Tomicus piniperda*);

Orthoptera: Asiatic locust (*Locusta migratoria*), African mole cricket (*Gryllotalpa africana*), rice grasshopper (*Oxya yezoensis*), and rice grasshopper (*Oxya japonica*);

Hymenoptera: Cabbage sawfly (*Athalia rosae*), leaf-cutting ant (*Acromyrmex* spp.), and fire ant (*Solenopsis* spp.);

Blattaria: German cockroach (*Blattella germanica*), smokybrown cockroach (*Periplaneta fuliginosa*), american cockroach (*Periplaneta americana*), brown cockroach (*Periplaneta brunnea*), and oriental cockroach (*Blatta orientalis*);

Acarina: spider mites such as two-spotted spider mite (*Tetranychus urticae*), citrus red mite (*Panonychus citri*), and *Oligonychus* spp.; eriophyid mites such as pink citrus rust mite (*Aculops pelekassi*); tarosonemid mites such as broad mite (*Polyphagotarsonemus latus*); false spider mites; peacock mites; flour mites such as mould mite (*Tyrophagus putrescentiae*); house dust mites such as American house dust mite (*Dermatophagoides farinae*), and European house dust mite (*Dermatophagoides ptrenyssnus*); and cheyletid mites such as *Cheyletus eruditus*, *Cheyletus malaccensis*, and *Cheyletus moorei*; and Nematodes: rice white-tip nematode (*Aphelenchoides besseyi*), strawberry bud nematode (*Nothotylenchus acris*), cotton root-knot nematode (*Meloidogyne incognita*) and cotton reniform nematode (*Rotylenchulus reniformis*).

Examples of plant diseases against which the composition for controlling pests of the present invention has control efficacy include the followings:

diseases of rice such as blast (*Magnaporthe grisea*), Helminthosporium leaf spot (*Cochliobolus miyabeanus*), sheath blight (*Rhizoctonia solani*), and bakanae disease (*Gibberella fujikuroi*);

diseases of wheat such as powdery mildew (*Erysiphe graminis*), *Fusarium* head blight (*Fusarium graminearum, F. avenacerum, F. culmorum, Microdochium nivale*), rust (*Puccinia striiformis, P. graminis, P. recondita*), pink snow mold (*Micronectriella nivale*), *Typhula* snow blight (*Typhula* sp.), loose smut (*Ustilago tritici*), bunt (*Tilletia caries*), eyespot (*Pseudocercosporella herpotrichoides*), leaf blotch (*Mycosphaerella graminicola*), glume blotch (*Stagonospora nodorum*), and yellow spot (*Pyrenophora tritici-repentis*); diseases of barley such as powdery mildew (*Erysiphe graminis*), *Fusarium* head blight (*Fusarium graminearum, F. avenacerum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), and *Rhizoctonia* damping-off (*Rhizoctonia solani*);

diseases of corn such as smut (*Ustilago maydis*), brown spot (*Cochliobolus heterostrophus*), copper spot (*Gloeocercospora sorghi*), southern rust (*Puccinia polysora*), gray leaf spot (*Cercospora zeae-maydis*), and *Rhizoctonia* damping-off (*Rhizoctonia solani*);

diseases of citrus such as melanose (*Diaporthe citri*), scab (*Elsinoe fawcetti*), penicillium rot (*Penicillium digitatum, P. italicum*), and brown rot (*Phytophthora parasitica, Phytophthora citrophthora*);

diseases of apple such as blossom blight (*Monilinia mali*), canker (*Valsa ceratosperma*), powdery mildew (*Podosphaera leucotricha*), *Alternaria* leaf spot (*Alternaria alternata* apple pathotype), scab (*Venturia inaequalis*), bitter rot (*Colletotrichum acutatum*), crown rot (*Phytophtora cactorum*), blotch (*Diplocarpon mali*), ring rot (*Botryosphaeria berengeriana*), and violet root rot (*Helicobasidium mompa*);

diseases of pear such as scab (*Venturia nashicola, V. pirina*), black spot (*Alternaria alternata* Japanese pear pathotype), rust (*Gymnosporangium haraeanum*), and *phytophthora* fruit rot (*Phytophtora cactorum*);

diseases of peach such as brown rot (*Monilinia fructicola*), scab (*Cladosporium carpophilum*), and *phomopsis* rot (*Phomopsis* sp.);

diseases of grape such as anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*);

diseases of Japanese persimmon such as anthracnose (*Gloeosporium kaki*), and leaf spot (*Cercospora kaki, Mycosphaerella nawae*);

diseases of gourd such as anthracnose (*Colletotrichum lagenarium*), powdery mildew (*Sphaerotheca fuliginea*), gummy stem blight (*Mycosphaerella melonis*), Fusarium wilt (*Fusarium oxysporum*), downy mildew (*Pseudoperonospora cubensis*), Phytophthora rot (*Phytophthora* sp.), and damping-off (*Pythium* sp.);

diseases of tomato such as early blight (*Alternaria solani*), leaf mold (*Cladosporium fulvum*), and late blight (*Phytophthora infestans*);

diseases of eggplant such as brown spot (*Phomopsis vexans*), and powdery mildew (*Erysiphe cichoracearum*).

diseases of cruciferous vegetables: Alternaria leaf spot (*Alternaria japonica*), white spot (*Cercosporella brassicae*), clubroot (*Plasmodiophora brassicae*), and downy mildew (*Peronospora parasitica*);

diseases of welsh onion such as rust (*Puccinia allii*), and downy mildew (*Peronospora destructor*);

diseases of soybean such as purple seed stain (*Cercospora kikuchii*), sphaceloma scad (*Elsinoe glycines*), pod and stem blight (*Diaporthe phaseolorum* var. *sojae*), septoria brown spot (*Septoria glycines*), frogeye leaf spot (*Cercospora sojina*), rust (*Phakopsora pachyrhizi*), brown stem rot (*Phytophthora sojae*), and Rhizoctonia damping-off (*Rhizoctonia solani*);

diseases of kidney bean such as anthracnose (*Colletotrichum lindemthianum*);

diseases of peanut such as leaf spot (*Cercospora personata*), brown leaf spot (*Cercospora arachidicola*) and southern blight (*Sclerotium rolfsii*);

diseases of garden pea such as powdery mildew (*Erysiphe pisi*), and root rot (*Fusarium solani f.* sp. *pisi*);

diseases of potato such as early blight (*Alternaria solani*), late blight (*Phytophthora infestans*), pink rot (*Phytophthora erythroseptica*), powdery scab (*Spongospora subterranean f.* sp. *subterranea*), and black scurf (*Rhizoctonia solani*);

diseases of strawberry such as powdery mildew (*Sphaerotheca humuli*), and anthracnose (*Glomerella cingulata*);

diseases of tea such as net blister blight (*Exobasidium reticulatum*), white scab (*Elsinoe leucospila*), gray blight (*Pestalotiopsis* sp.), and anthracnose (*Colletotrichum theaesinensis*);

diseases of tobacco such as brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*);

diseases of rapeseed such as *sclerotinia* rot (*Sclerotinia sclerotiorum*), and *Rhizoctonia* damping-off (*Rhizoctonia solani*);

diseases of cotton such as *Rhizoctonia* damping-off (*Rhizoctonia solani*);

diseases of sugar beet such as *Cercospora* leaf spot (*Cercospora beticola*), leaf blight (*Rhizoctonia solani*), Root rot (*Rhizoctonia solani*), and *Aphanomyces* root rot (*Aphanomyces cochlioides*);

diseases of rose such as black spot (*Diplocarpon rosae*), powdery mildew (*Sphaerotheca pannosa*), and downy mildew (*Peronospora sparsa*);

diseases of chrysanthemum and asteraceous plants such as downy mildew (*Bremia lactucae*), leaf blight (*Septoria chrysanthemi-indici*), and white rust (*Puccinia horiana*).

diseases of various groups such as diseases caused by *Pythium* spp. (*Pythium debarianum, Pythium graminicola, Pythium irregulare, Pythium ultimum*), gray mold (*Botrytis cinerea*), *Sclerotinia* rot (*Sclerotinia sclerotiorum*), or southern blight (*Sclerotium rolfsii*);

disease of Japanese radish such as *Alternaria* leaf spot (*Alternaria brassicicola*);

diseases of turfgrass such as dollar spot (*Sclerotinia homeocarpa*), and brown patch and large patch (*Rhizoctonia solani*);

disease of banana such as sigatoka (*Mycosphaerella fijiensis, Mycosphaerella musicola*);

disease of sunflower such as downy mildew (*Plasmopara halstedii*);

seed diseases or diseases in the early stages of the growth of various plants caused by *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Phoma* spp., *Rhizoctonia* spp. or *Diplodia* spp.; and viral diseases of various plants mediated by *Polymixa* spp. or *Olpidium* spp.

In the case of treatment of seed, bulb or the like, examples of plant diseases for which high control efficacy of the present invention is expected include:

damping-off and root rot of wheat, barley, corn, rice, sorghum, soybean, cotton, rapeseed, sugar beet and turfgrass caused by *Pythium* spp. (*Pythium debarianum, Pythium graminicola, Pythium irregulare, Pythium ultimum*);

*Aphanomyces* root rot (*Aphanomyces cochlioides*) of sugar beet;

brown stem rot (*Phytophthora sojae*) of soybean;

black shank (*Phytophthora nicotianae*) of tobacco;

downy mildew (*Plasmopara halstedii*) of sunflower; and late blight (*Phytophthora infestans*) of potato.

Pests can be controlled by applying effective amounts of ethaboxam and avermectin to the pests or to such a place as plant and soil where the pests inhabit or may inhabit.

Pests can be controlled and plants can be protected from damages from pests by applying effective amounts of ethaboxam and avermectin to a plant or soil for growing plant. Examples of a plant which is the object of the application include foliages of plant, seeds of plant, bulbs of plant. As used herein, the bulb means a bulb, corm, rhizoma, stem tuber, root tuber and rhizophore.

When the application is conducted to pests, a plant or the soil for growing plant, ethaboxam and avermectin may be separately applied for the same period, but they are typically applied as a composition for controlling pests of the present invention for simplicity of the application.

Examples of the controlling method of the present invention include treatment of foliage of plants, such as foliage application; treatment of cultivation lands of plants, such as soil treatment; treatment of seeds, such as seed sterilization and seed coating; and treatment of bulbs such as seed tuber.

Examples of the treatment of foliage of plants in the controlling method of the present invention include treatment methods of applying to surfaces of plants, such as foliage spraying and trunk spraying. Examples of the treatment method of directly absorbing to plants before transplantation include a method of soaking entire plants or roots. A formulation obtained by using a solid carrier such as a mineral powder may be adhered to the roots.

Examples of the soil treatment method in the controlling method of the present invention include spraying onto the soil, soil incorporation, and perfusion of a chemical liquid into the soil (irrigation of chemical liquid, soil injection, and dripping of chemical liquid). Examples of the place to be treated include planting hole, furrow, around a planting hole, around a furrow, entire surface of cultivation lands, the parts between the soil and the plant, area between roots, area beneath the trunk, main furrow, growing soil, seedling raising box, seedling raising tray and seedbed. Examples of the treating period include before seeding, at the time of seeding, immediately after seeding, raising period, before settled planting, at the time of settled planting, and growing period after settled planting. In the above soil treatment, active ingredients may be simultaneously applied to the plant, or a solid fertilizer such as a paste fertilizer containing active ingredients may be applied to the soil. Also active ingredients may be mixed in an irrigation liquid, and, examples thereof include injecting to irrigation facilities such as irrigation tube, irrigation pipe and sprinkler, mixing into the flooding liquid between furrows and mixing into a water culture medium. Alternatively, an irrigation liquid is mixed with active ingredients in advance and, for example, used for treatment by an appropriate irrigating method including the irrigating method mentioned above and the other methods such as sprinkling and flooding.

Examples of the method of treating seeds or bulbs in the controlling method of the present invention include a method for treating seeds or bulbs to be protected from pests with the composition for controlling pests of the present invention and specific examples thereof include a spraying treatment in which a suspension of the composition for controlling pests of the present invention is atomized and sprayed on the seed surface or the bulb surface; a smearing treatment in which a wettable powder, an emulsion or a flowable agent of the composition for controlling pests of the present invention is applied to seeds or bulbs with a small amount of water added or without dilution; an immersing treatment in which seeds are immersed in a solution of the composition for controlling pests of the present invention for a certain period of time; film coating treatment; and pellet coating treatment.

When a plant or soil for growing plant is treated with ethaboxam and avermectin, the amounts of ethaboxam and avermectin used for the treatment may be changed depending on the kind of the plant to be treated, the kind and the occurring frequency of the pests to be controlled, formulation form, treatment period, climatic condition and so on, but the total amount of ethaboxam and avermectin (hereinafter, referred to as the amount of the active ingredients) per 10,000 m$^2$ is typically 1 to 5,000 g and preferably 2 to 500 g.

The emulsion, wettable powder and flowable agent are typically diluted with water, and then sprinkled for the treatment. In these case, the total concentration of the ethaboxam and avermectin is typically in the range of 0.0001 to 3% by weight and preferably 0.0005 to 1% by weight. The powder agent and granule agent are typically used for the treatment without being diluted.

In the treatment of seeds, the amount of the active ingredients to be applied is typically in the range of 0.001 to 10 g, preferably 0.01 to 3 g per 1 kg of seeds.

The control method of the present invention can be used in agricultural lands such as fields, paddy fields, lawns and orchards or in non-agricultural lands.

The present invention can be used to control pests in agricultural lands for cultivating the following "plant" and the like without adversely affecting the plant and so on.

Examples of the plants are as follows:

crops such as corn, rice, wheat, barley, rye, oat, sorghum, cotton, soybean, peanut, buckwheat, beet, rapeseed, sunflower, sugar cane, and tobacco;

vegetables such as solanaceous vegetables including eggplant, tomato, pimento, pepper and potato, cucurbitaceous vegetables including cucumber, pumpkin, zucchini, water melon, melon and squash, cruciferous vegetables including Japanese radish, white turnip, horseradish, kohlrabi, Chinese cabbage, cabbage, leaf mustard, broccoli and cauliflower, asteraceous vegetables including burdock, crown daisy, artichoke and lettuce, liliaceous vegetables including green onion, onion, garlic and asparagus, ammiaceous vegetables including carrot, parsley, celery and parsnip, chenopodiaceous vegetables including spinach and Swiss chard, lamiaceous vegetables including *Perilla frutescens*, mint and basil, strawberry, sweet potato, *Dioscorea japonica*, and *colocasia*;

flowers;

foliage plants;

turf grasses;

fruits such as pomaceous fruits including apple, pear, Japanese pear, Chinese quince and quince, stone fleshy fruits including peach, plum, nectarine, Prunus mume, cherry fruit, apricot and prune, citrus fruits including Citrus unshiu, orange, lemon, rime and grapefruit, nuts including chestnuts, walnuts, hazelnuts, almond, pistachio, cashew nuts and macadamia nuts, berries including blueberry, cranberry, blackberry and raspberry, grape, kaki fruit, olive, Japanese plum, banana, coffee, date palm, and coconuts; and trees other than fruit trees such as tea, mulberry, flowering plant, and roadside trees including ash, birch, dogwood, Eucalyptus, Ginkgo biloba, lilac, maple, Quercus, poplar, Judas tree, Liquidambar formosana, plane tree, zelkova, Japanese arborvitae, fir wood, hemlock, juniper, Pinus, Picea, and Taxus cuspidate.

Particularly, the control method of the present invention can be used to control diseases in agricultural lands for cultivating corn, rice, wheat, barley, sorghum, cotton, soybean, beet, rapeseed, turf grasses or potato.

The aforementioned "plants" include plants, to which resistance to HPPD inhibitors such as isoxaflutole, ALS inhibitors such as imazethapyr or thifensulfuron-methyl, EPSP synthetase inhibitors such as glyphosate, glutamine synthetase inhibitors such as the glufosinate, acetyl-CoA carboxylase inhibitors such as sethoxydim, and herbicides such as bromoxynil, dicamba, 2,4-D, etc. has been conferred by a classical breeding method or genetic engineering technique.

Examples of a "plant" on which resistance has been conferred by a classical breeding method include rape, wheat, sunflower and rice resistant to imidazolinone ALS inhibitory herbicides such as imazethapyr, which are already commercially available under a product name of Clearfield (registered trademark). Similarly, there is soybean on which resistance to sulfonylurea ALS inhibitory herbicides such as thifensulfuron-methyl has been conferred by a classical breeding method, which is already commercially available under a product name of STS soybean. Similarly, examples on which resistance to acetyl-CoA carboxylase inhibitors such as trione oxime or aryloxy phenoxypropionic acid herbicides has been conferred by a classical breeding method include SR corn. The plant on which resistance to acetyl-CoA carboxylase inhibitors has been conferred is described in Proceedings of the National Academy of Sciences of the United States of America (Proc. Natl. Acad. Sci. USA), vol. 87, pp. 7175-7179 (1990). A variation of acetyl-CoA carboxylase resistant to an acetyl-CoA carboxylase inhibitor is reported in Weed Science, vol. 53, pp. 728-746 (2005) and a plant resistant to acetyl-CoA carboxylase inhibitors can be generated by introducing a gene of such an acetyl-CoA carboxylase variation into a plant by genetically engineering technology, or by introducing a variation conferring resistance into a plant acetyl-CoA carboxylase. Furthermore, plants resistant to acetyl-CoA carboxylase inhibitors or ALS inhibitors or the like can be generated by introducing a site-directed amino acid substitution variation into an acetyl-CoA carboxylase gene or the ALS gene of the plant by introduction a nucleic acid into which has been introduced a base substitution variation represented Chimeraplasty Technique (Gura T. 1999. Repairing the Genome's Spelling Mistakes. Science 285: 316-318) into a plant cell.

Examples of a plant on which resistance has been conferred by genetic engineering technology include corn, soybean, cotton, rape, sugar beet resistant to glyphosate, which is already commercially available under a product name of RoundupReady (registered trademark), AgrisureGT, etc. Similarly, there are corn, soybean, cotton and rape which are made resistant to glufosinate by genetic engineering technology, a kind, which is already commercially available under a product name of LibertyLink (registered trademark). A cotton made resistant to bromoxynil by genetic engineering technology is already commercially available under a product name of BXN likewise.

The aforementioned "plants" include genetically engineered crops produced using such genetic engineering techniques, which, for example, are able to synthesize selective toxins as known in genus *Bacillus*.

Examples of toxins expressed in such genetically engineered crops include: insecticidal proteins derived from *Bacillus cereus* or *Bacillus popilliae*; δ-endotoxins such as Cry1Ab, Cry1Ac, Cry1F, Cry1Fa2, Cry2Ab, Cry3A, Cry3Bb1 or Cry9C, derived from *Bacillus thuringiensis*; insecticidal proteins such as VIP1, VIP2, VIP3, or VIP3A; insecticidal proteins derived from nematodes; toxins generated by animals, such as scorpion toxin, spider toxin, bee toxin, or insect-specific neurotoxins; mold fungi toxins; plant lectin; agglutinin; protease inhibitors such as a trypsin inhibitor, a serine protease inhibitor, patatin, cystatin, or a papain inhibitor; ribosome-inactivating proteins (RIP) such as lycine, corn-RIP, abrin, luffin, saporin, or briodin; steroid-metabolizing enzymes such as 3-hydroxysteroid oxidase, ecdysteroid-UDP-glucosyl transferase, or cholesterol oxidase; an ecdysone inhibitor; HMG-COA reductase; ion channel inhibitors such as a sodium channel inhibitor or calcium channel inhibitor; juvenile hormone esterase; a diuretic hormone receptor; stilbene synthase; bibenzyl synthase; chitinase; and glucanase.

Toxins expressed in such genetically engineered crops also include: hybrid toxins of δ-endotoxin proteins such as Cry1Ab, Cry1Ac, Cry1F, Cry1Fa2, Cry2Ab, Cry3A, Cry3Bb1, Cry9C, Cry34Ab or Cry35Ab and insecticidal proteins such as VIP1, VIP2, VIP3 or VIP3A; partially deleted toxins; and modified toxins. Such hybrid toxins are produced from a new combination of the different domains of such proteins, using a genetic engineering technique. As a partially deleted toxin, Cry1Ab comprising a deletion of a portion of an amino acid sequence has been known. A modified toxin is produced by substitution of one or multiple amino acids of natural toxins.

Examples of such toxins and genetically engineered plants capable of synthesizing such toxins are described in EP-A-0 374 753, WO 93/07278, WO 95/34656, EP-A-0 427 529, EP-A-451 878, WO 03/052073, etc.

Toxins contained in such genetically engineered plants are able to confer resistance particularly to insect pests belonging to Coleoptera, Hemiptera, Diptera, Lepidoptera and Nematodes, to the plants.

Genetically engineered plants, which comprise one or multiple insecticidal pest-resistant genes and which express one or multiple toxins, have already been known, and some of such genetically engineered plants have already been on the market. Examples of such genetically engineered plants include YieldGard (registered trademark) (a corn variety for expressing Cry1Ab toxin), YieldGard Rootworm (registered trademark) (a corn variety for expressing Cry3Bb1 toxin), YieldGard Plus (registered trademark) (a corn variety for expressing Cry1Ab and Cry3Bb1 toxins), Herculex I (registered trademark) (a corn variety for expressing phosphinotricine N-acetyl transferase (PAT) so as to confer resistance to Cry1Fa2 toxin and glufosinate), NuCOTN33B (registered trademark) (a cotton variety for expressing Cry1Ac toxin), Bollgard I (registered trademark) (a cotton variety for expressing Cry1Ac toxin), Bollgard II (registered trademark) (a cotton variety for expressing Cry1Ac and Cry2Ab toxins), VIPCOT (registered trademark) (a cotton variety for expressing VIP toxin), NewLeaf (registered trademark) (a potato variety for expressing Cry3A toxin), NatureGard (registered trademark) Agrisure (registered trademark) GT Advantage (GA21 glyphosate-resistant trait), Agrisure (registered trademark) CB Advantage (Bt11 corn borer (CB) .trait), and Protecta (registered trademark).

The aforementioned "plants" also include crops produced using a genetic engineering technique, which have ability to generate antipathogenic substances having selective action.

A PR protein and the like have been known as such antipathogenic substances (PRPs, EP-A-0 392 225). Such antipathogenic substances and genetically engineered crops that generate them are described in EP-A-0 392 225, WO 95/33818, EP-A-0 353 191, etc.

Examples of such antipathogenic substances expressed in genetically engineered crops include: ion channel inhibitors such as a sodium channel inhibitor or a calcium channel inhibitor (KP1, KP4 and KP6 toxins, etc., which are produced by viruses, have been known); stilbene synthase; bibenzyl synthase; chitinase; glucanase; a PR protein; and antipathogenic substances generated by microorganisms, such as a peptide antibiotic, an antibiotic having a hetero ring, a protein factor associated with resistance to plant diseases (which is called a plant disease-resistant gene and is described in WO 03/000906). These antipathogenic substances and genetically engineered plants producing such substances are described in EP-A-0392225, WO95/33818, EP-A-0353191, etc.

The "plant" mentioned above includes plants on which advantageous characters such as characters improved in oil stuff ingredients or characters having reinforced amino acid content have been conferred by genetically engineering technology. Examples thereof include VISTIVE (registered trademark) low linolenic soybean having reduced linolenic content) or high-lysine (high-oil) corn (corn with increased lysine or oil content). The "plant" mentioned above also includes plants on which tolerance to environmental stress such as drought stress, salt stress, heat stress, cold stress, pH stress, light stress, or stress caused by soil pollution with heavy metals has been conferred by genetic engineering technology.

Stack varieties are also included in which are combined a plurality of advantageous characters such as the classic herbicide characters mentioned above or herbicide tolerance genes, harmful insect resistance genes, antipathogenic substance producing genes, characters improved in oil stuff ingredients or characters having reinforced amino acid content, and environmental stress tolerance genes.

EXAMPLES

While the present invention will be more specifically described by way of formulation examples, seed treatment examples, and test examples in the following, the present invention is not limited to the following examples. In the following examples, the part represents part by weight unless otherwise noted in particular.

Formulation Example 1

Fully mixed are 0.5 parts of ethaboxam, 3 parts of avermectin, 14 parts of polyoxyethylene styrylphenyl ether, 6 parts of calcium dodecyl benzene sulfonate and 76.5 parts of xylene, so as to obtain an emulsion.

Formulation Example 2

Two (2) parts of ethaboxam, 8 parts of avermectin, 35 parts of a mixture of white carbon and a polyoxyethylene alkyl ether sulfate ammonium salt (weight ratio 1:1) and 55 parts of water are mixed, and the mixture is subjected to fine grinding according to a wet grinding method, so as to obtain a flowable formulation.

Formulation Example 3

Two (2) parts of ethaboxam, 10 parts of avermectin, 1.5 parts of sorbitan trioleate and 31.5 parts of an aqueous solution containing 2 parts of polyvinyl alcohol are mixed, and the mixture is subjected to fine grinding according to a wet grinding method. Thereafter, 45 parts of an aqueous solution containing 0.05 part of Xanthan gum and 0.1 part of aluminum magnesium silicate is added to the resultant mixture, and 10 parts of propylene glycol is further added thereto. The obtained mixture is blended by stirring, so as to obtain a flowable formulation.

Formulation Example 4

Five (5) parts of ethaboxam, 40 parts of avermectin, 5 parts of propylene glycol (manufactured by Nacalai Tesque), 5 parts of SoprophorFLK (manufactured by Rhodia Nikka), 0.2 parts of an anti-form C emulsion (manufactured by Dow Corning), 0.3 parts of proxel GXL (manufactured by Arch Chemicals) and 49.5 parts of ion-exchange water are mixed so as to obtain a bulk slurry. 150 parts of glass beads (diameter=1 mm) are put into 100 parts of the slurry, and the slurry is ground for 2 hours while being cooled with a cooling water. After ground, the resultant is filtered to remove the glass beads and a flowable formulation is obtained.

Formulation Example 5

Ten (10) parts of ethaboxam, 40 parts of avermectin, 38.5 parts of NN kaolin clay (manufactured by Takehara Chemical Industrial), 10 parts of MorwetD425 and 1.5 parts of MorwerEFW (manufactured by Akzo Nobel Corp.) are mixed to obtain an AI premix. This premix is ground with a jet mill so as to obtain a powder formulation.

Formulation Example 6

Two (2) parts of ethaboxam, 3 parts of avermectin, 1 part of synthetic hydrated silicon oxide, 2 parts of calcium lignin sulfonate, 30 parts of bentonite and 62 parts of kaolin clay are fully ground and mixed, and the resultant mixture is added with water and fully kneaded, and then subjected to granulation and drying so as to obtain a granule formulation.

Formulation Example 7

Fifteen (15) parts of ethaboxam, 20 parts of avermectin, 3 parts of calcium lignin sulfonate, 2 parts of sodium lauryl sulfate and 60 parts of synthetic hydrated silicon oxide are fully ground and mixed so as to obtain wettable powders.

Formulation Example 8

One (1) part of ethaboxam, 5 parts of avermectin, 84 parts of kaolin clay and 10 parts of talc are fully ground and mixed so as to obtain a powder formulation.

Seed Treatment Example 1

An emulsion prepared as in Formulation example 1 is used for smear treatment in an amount of 500 ml per 100 kg of dried sorghum seeds using a rotary seed treatment machine (seed dresser, produced by Hans-Ulrich Hege GmbH) so as to obtain treated seeds.

Seed Treatment Example 2

A flowable formulation prepared as in Formulation example 2 is used for smear treatment in an amount of 50 ml per 10 kg of dried rape seeds using a rotary seed treatment machine (seed dresser, produced by Hans-Ulrich Hege GmbH) so as to obtain treated seeds.

Seed Treatment Example 3

A flowable formulation prepared as in Formulation example 3 is used for smear treatment in an amount of 40 ml per 10 kg of dried corn seeds using a rotary seed treatment machine (seed dresser, produced by Hans-Ulrich Hege GmbH) so as to obtain treated seeds.

Seed Treatment Example 4

Five (5) parts of a flowable formulation prepared as in Formulation example 4, 5 parts of pigment BPD6135 (manufactured by Sun Chemical) and 35 parts of water are mixed to prepare a mixture. The mixture is used for smear treatment in an amount of 60 ml per 10 kg of dried rice seeds using a rotary seed treatment machine (seed dresser, produced by Hans-Ulrich Hege GmbH) so as to obtain treated seeds.

Seed Treatment Example 5

A powder agent prepared as in Formulation example 5 is used for powder coating treatment in an amount of 50 g per 10 kg of dried corn seeds so as to obtain treated seeds.

Seed Treatment Example 6

An emulsion prepared as in Formulation example 1 is used for smear treatment in an amount of 500 ml per 100 kg of dried sugar beet seeds using a rotary seed treatment machine (seed dresser, produced by Hans-Ulrich Hege GmbH) so as to obtain treated seeds.

Seed Treatment Example 7

A flowable formulation prepared as in Formulation example 2 is used for smear treatment in an amount of 50 ml per 10 kg of dried soybean seeds using a rotary seed treatment machine (seed dresser, produced by Hans-Ulrich Hege GmbH) so as to obtain treated seeds.

Seed Treatment Example 8

A flowable formulation prepared as in Formulation example 3 is used for smear treatment in an amount of 50 ml per 10 kg of dried wheat seeds using a rotary seed treatment machine (seed dresser, produced by Hans-Ulrich Hege GmbH) so as to obtain treated seeds.

Seed Treatment Example 9

Five (5) parts of a flowable formulation prepared as in Formulation example 4, 5 parts of pigment BPD6135 (manufactured by Sun Chemical) and 35 parts of water are mixed and the resultant mixture is used for smear treatment in an amount of 70 ml per 10 kg of potato tuber pieces using a rotary seed treatment machine (seed dresser, produced by Hans-Ulrich Hege GmbH) so as to obtain treated seeds.

Seed Treatment Example 10

Five (5) parts of a flowable formulation prepared as in Formulation example 4, 5 parts of pigment BPD6135 (manufactured by Sun Chemical) and 35 parts of water are mixed and the resultant mixture is used for smear treatment in an amount of 70 ml per 10 kg of sunflower seeds using a rotary seed treatment machine (seed dresser, produced by Hans-Ulrich Hege GmbH) so as to obtain treated seeds.

Seed Treatment Example 11

A powder prepared as in Formulation example 5 is used for powder coating treatment in an amount of 40 g per 10 kg of dried cotton seeds so as to obtain treated seeds.

Test Example 1

A dimethylsulfoxide (hereinafter, abbreviated to as DMSO) solution of ethaboxam and a DMSO solution of avermectin B were respectively prepared, and these solutions were mixed to prepare a DMSO mixed solution containing 1% by weight of ethaboxam and 1% by weight of avermectin B. Five (5) g of corn (Pioneer) seeds and 12.5 µL of the DMSO mixed solution were mixed by shaking in a 50-ml conical tube and then allowed to stand overnight to prepare treated seeds. A plastic pot was filled with sandy soil and the treated seeds were sown on it and then covered with sandy soil which had been mixed with a bran culture of *Pythium* damping-off pathogen (*Pythium irregulare*). The sown seeds were watered and then cultured at 15° C. under humidity for 2 weeks. The number of emerging corn seedlings was checked and the incidence of disease was calculated by Equation 1.

In order to calculate a control value, the incidence of disease was also checked in the case in which the seeds had not been treated with the test compounds.

The control value was calculated by the Equation 2 based on the incidence of disease thus determined.

The results are shown in Table 1.

Incidence of disease={(Total number of sowed seeds)−(Number of emerging seedlings}×100/ (Total number of sowed seeds)  "Equation 1"

Control value=100×(*A*−*B*)/*A*  "Equation 2"

A: Incidence of disease of plants treated with none of the test compounds
B: Incidence of disease of plants treated with the test compounds

TABLE 1

| Test compounds | Active ingredient dosage (g/100 kg seeds) | Control value |
|---|---|---|
| Ethaboxam + avermectin B | 2.5 + 2.5 | 86 |

Test Example 2

A DMSO solution of ethaboxam and a DMSO solution of avermectin B were respectively prepared, and these solutions were mixed to prepare a DMSO mixed solution containing 2% by weight of ethaboxam and 1% by weight of avermectin B. Ten (10) µL of the DMSO mixed solution and 1 g of cucumber (*Sagamihanjiro*) seeds were mixed by shaking in a 15-ml conical tube and then allowed to stand overnight to prepare treated seeds. A plastic pot was filled with sandy soil and the treated seeds were sown on it and then covered with sandy soil which had been mixed with a bran culture of *Pythium* damping-off pathogen (*Pythium irregulare*). The sown seeds were watered and then cultured at 18° C. under humidity for 1 week. The number of emerging cucumber seedlings was checked and the incidence of disease was calculated by Equation 1.

In order to calculate a control value, the incidence of disease was also checked in the case in which the seeds had not been treated with the test compounds.

The control value was calculated by the Equation 2 based on the incidence of disease thus determined.

The results are shown in Table 2.

TABLE 2

| Test compounds | Active ingredient dosage (g/100 kg seeds) | Control value |
|---|---|---|
| Ethaboxam + avermectin B | 10 + 5 | 100 |

Test Example 3

A DMSO solution of ethaboxam and a DMSO solution of avermectin are respectively prepared, and these solutions are mixed to prepare a DMSO mixed solution containing 2% by weight of ethaboxam and 1% by weight of avermectin and a DMSO mixed solution containing 1% by weight of ethaboxam and 1% by weight of avermectin. Twenty-five (25) µL of the respective DMSO mixed solution and 10 g of corn (Pioneer) seeds are mixed by shaking in a 50-ml conical tube and then allowed to stand overnight to prepare treated seeds. A plastic pot is filled with sandy soil and the treated seeds are sown on it and then covered with sandy soil which has been mixed with a bran culture of *Pythium* damping-off pathogen (*Pythium ultimum*). The sown seeds are watered and then cultured at 18° C. under humidity for 2 weeks, and control efficacy is checked. As a result, excellent efficacy for controlling the plant disease is observed in the respective seeds treated with ethaboxam and avermectin.

INDUSTRIAL APPLICABILITY

This invention is capable of providing a composition for controlling pests having excellent activity and a method for effectively controlling pests.

The invention claimed is:

1. A composition for controlling pests comprising ethaboxam and avermectin at a weight ratio of ethaboxam to avermectin in a range of 1:0.1 to 1:20.

2. A seed treatment agent comprising, as active ingredients, ethaboxam and avermectin at a weight ratio of ethaboxam to avermectin in a range of 1:0.1 to 1:20.

3. A plant seed treated with effective amounts of ethaboxam and avermectin at a weight ratio of ethaboxam to avermectin in a range of 1:0.1 to 1:20.

4. A method for controlling pests which comprises applying the composition of claim 1 to a pest, a plant or soil for growing plant.

* * * * *